US008877500B2

(12) United States Patent
Banes et al.

(10) Patent No.: US 8,877,500 B2
(45) Date of Patent: Nov. 4, 2014

(54) THERMALLY INDUCED GELATION OF COLLAGEN HYDROGEL AND METHOD OF THERMALLY INDUCING GELLING A COLLAGEN HYDROGEL

(71) Applicant: MedTrain Technologies, LLC, Hillsborough, NC (US)

(72) Inventors: Albert J. Banes, Hillsborough, NC (US); Mari Tsuzaki, Chapel Hill, NC (US); Jie Qi, Chapel Hill, NC (US)

(73) Assignee: MedTrain Technologies, LLC, Hillsborough, NC (US)

( * ) Notice: Subject to any disclaimer, the term of this patent is extended or adjusted under 35 U.S.C. 154(b) by 0 days.

(21) Appl. No.: 14/166,960

(22) Filed: Jan. 29, 2014

(65) Prior Publication Data
US 2014/0242696 A1     Aug. 28, 2014

Related U.S. Application Data

(62) Division of application No. 13/316,034, filed on Dec. 9, 2011, now Pat. No. 8,663,988.

(51) Int. Cl.
*C12N 5/00*     (2006.01)

(52) U.S. Cl.
CPC .......... *C12N 5/0068* (2013.01); *C12N 2500/30* (2013.01)
USPC .......................................... 435/397; 435/395

(58) Field of Classification Search
USPC ................................................. 435/397, 395
See application file for complete search history.

(56) References Cited

U.S. PATENT DOCUMENTS

| 4,349,026 A | 9/1982 | Miyata |
| 2004/0142411 A1 | 7/2004 | Kirk et al. |

OTHER PUBLICATIONS

Drake et al. (Action of Proteolytic Enzymes on Tropocollagen and Insoluble Collagen. Biochemistry. 1966 5(1): 301-312).*
Drake, et al., Action of Proteolytic Enzymes on Tropocollagen and Insoluble Collagen, Biochemistry, Jan. 1966, pp. 301-312, vol. 5, No. 1.
Fledelius, et al., Characterization of Urinary Degradation Products Derived from Type I Collagen—Identification of a β-Isomerized Asp-Gly Sequence within the C-Terminal Telopeptide (α1) Region, The Journal of Biological Chemistry, 1997, pp. 9755-9763, vol. 272, No. 15.
Garvin, et al., Novel System for Engineering Bioartificial Tendons and Application of Mechanical Load, Tissue Engineering, 2003, pp. 967-979, vol. 9, No. 5.
Lynn, et al., Antigenicity and Immunogenicity of Collagen, Journal of Biomedical Materials Research Part B: Applied Biomaterials, 2004, pp. 343-354, vol. 71B.
Mi, et al., In Vivo Biocompatibility and Degradability of a Novel Injectable-Chitosan-Based Implant, Biomaterials, 2002, pp. 181-191, vol. 23.
Mwale, et al., Biological Evaluation of Chitosan Salts Cross-Linked to Genipin as a Cell Scaffold for Disk Tissue Engineering, Tissue Engineering, 2005, pp. 130-140, vol. 11, No. 1/2.
Prabaharan, et al., Chitosan-graft-β-Cyclodextrin Scaffolds with Controlled Drug Release Capability for Tissue Engineering Applications, International Journal of Biological Macromolecules, 2009, pp. 320-325, vol. 44.
Qi, et al., Interleukin-1β Increases Elasticity of Human Bioartificial Tendons, Tissue Engineering, 2006, pp. 2913-2925, vol. 12, No. 10.
Qi, et al., Modulation of Collagen Gel Compaction by Extracellular ATP is MAPK and NF-κB Pathways Dependent, Experimental Cell Research, 2009, pp. 1990-2000, vol. 315.
Qi, et al., ATP Reduces Gel Compaction in Osteoblast-Populated Collagen Gels, J Appl Physiol, 2007, pp. 1152-1160, vol. 102.
Qi, et al., Chitosan-Doped Collagen Hydrogels: Reduced 3D Gel Compaction by Stem Cells, Biomedical Engineering, Poster presented at the 50th American Society for Cell Biology Annual Meeting, Philadelphia PA, Dec. 11-15, 2010, 1 page.
Shoulders, et al., Collagen Structure and Stability, Published in final edited form as: Annual Review of Biochemistry, 2009, pp. 929-958, vol. 78.
Sung, et al., Evaluation of Gelatin Hydrogel Crosslinked with Various Crosslinking Agents as Bioadhesives: In Vitro Study, Journal of Biomedical Materials Research, 1999, pp. 520-530, vol. 46.
Sweeney, et al., Candidate Cell and Matrix Interaction Domains on the Collagen Fibril, the Predominant Protein of Vertebrates, Journal of Biological Chemistry, 2008, pp. 21187-21197, vol. 283, No. 30.

* cited by examiner

*Primary Examiner* — Karen Cochrane Carlson
*Assistant Examiner* — Natalie Moss
(74) *Attorney, Agent, or Firm* — The Webb Law Firm

(57) ABSTRACT

The present invention relates to collagen hydrogels. Particularly, the invention relates to hydrogels comprising a telopeptide collagen ("telo-collagen") and an atelopeptide collagen ("atelo-collagen"); hydrogels comprising collagen and chitosan; methods of making the hydrogels; methods of reducing gelation of a hydrogel mixture at room temperature; methods of reducing compaction of cells; and methods of culturing cells on such hydrogels.

8 Claims, 24 Drawing Sheets

US 8,877,500 B2

THERMALLY INDUCED GELATION OF COLLAGEN HYDROGEL AND METHOD OF THERMALLY INDUCING GELLING A COLLAGEN HYDROGEL

CROSS REFERENCE TO RELATED APPLICATIONS

This application is a division of U.S. application Ser. No. 13/316,034, filed Dec. 9, 2011, which is hereby incorporated by reference in its entirety.

FIELD OF THE INVENTION

The present invention relates to collagen hydrogels. Particularly, the invention relates to hydrogels comprising a telopeptide-collagen and an atelopeptide-collagen; hydrogels comprising collagen and chitosan; methods of making the hydrogels; methods of reducing gelation of a hydrogel mixture at room temperature; methods of reducing compaction of cells; and methods of culturing cells on such hydrogels.

BACKGROUND OF THE INVENTION

Collagen hydrogels are in broad use in today's clinical, tissue engineering and cell biology fields as scaffolds, labware coating, cell encapsulation materials and injectables. Most of the commercial preparations are pepsin-treated atelopeptide type I collagen preparations lacking the fibril associating C-terminus and do not form native-like fibrils. One commercially important collagen product for cell culture/tissue engineering is Purecol® from Inamed Inc. (now Advanced Biomolecules). Purecol® is a type I, monomeric collagen extracted from bovine hide, with telopeptide ends partially removed. Monomeric collagen forms a random fibrillar network with fewer cross-links compared to polymeric collagen, is weaker and has a slower gelation time (30-120 min). The latter properties limit its applications in fields such as tissue engineering, cell encapsulation, and clinical applications, where high mechanical strength and/or rapid gelation time (minutes) are required. Another disadvantage of bovine collagen products is the potential for contamination with bovine spongiform encephalopathy (BSE) virus, or Mad Cow Disease, which is transmissible to humans.

SUMMARY OF THE INVENTION

The invention relates to a family of robust, collagen-based hydrogels with a more organized fibrillar network and controlled gelation rates. These improved hydrogels yield better performance in the applications of tissue engineering and cell encapsulation.

In one aspect, the invention is a hydrogel mixture comprising a telopeptide-containing-collagen and an atelopeptide-containing-collagen. The telopeptide-containing-collagen represents 5-25 weight percent of the total collagen in the hydrogel. The atelopeptide-collagen represents 75-95 weight percent of the total collagen in the hydrogel. Optionally, the hydrogel may further comprise chitosan and/or genipin.

In another aspect, the invention is a method of fabricating a hydrogel. The method comprises combining a telopeptide-collagen and an atelopeptide-collagen to form a mixture. The mixture has a total amount of collagen. The telopeptide-collagen represents 5-25 weight percent of the total amount of collagen in the hydrogel. The atelopeptide-collagen represents 75-95 weight percent of the total amount of collagen in the hydrogel. The mixture is heated. Optionally, the hydrogel may further comprise chitosan.

In another aspect, the invention is directed to a method of reducing gelation of a hydrogel containing a telopeptide-collagen at room temperature. The method comprises mixing a telopeptide-collagen and an atelopeptide-collagen to form a collagen mixture. The telopeptide-collagen represents 5-25 weight percent of the total amount of collagen in the hydrogel. The mixture has a total amount of collagen. The atelopeptide-collagen represents 75-95 weight percent of the total amount of collagen in the hydrogel. The mixture is stored at a temperature less than about 37° C. Gelation of the collagen mixture is reduced at this temperature.

In another aspect, the invention is a method of culturing cells. The method comprises providing a hydrogel. The hydrogel comprising a telopeptide-collagen and an atelopeptide-collagen. The telopeptide-collagen represents 5-25 weight percent of the total collagen in the hydrogel. The atelopeptide-collagen represents 75-95 weight percent of the total collagen in the hydrogel. The cells are cultured on the hydrogel.

Another aspect of the invention is directed to a hydrogel. The hydrogel comprises a collagen and a chitosan.

In another aspect, the invention is a method of reducing cell driven compaction in hydrogel. The method comprises forming a hydrogel comprising a collagen and a chitosan. Cells are cultured on the hydrogel, and have reduced compaction.

In another aspect, the invention is a method of reducing fibril compaction in a hydrogel. The method comprises polymerizing a composition comprising a collagen and chitosan, and optionally genipin.

DESCRIPTION OF THE FIGURES

FIG. 20A is the cross-section view of reconstructed 3D images of collagen gels. Cells were stained with rhodamine-phalloidin. FIG. 20B is live-dead cells staining. Red cells are dead cells. FIG. 20C is the growth curves of MG63 cells grown in 3D collagen gels.

DETAILED DESCRIPTION OF THE INVENTION

Figure 1:
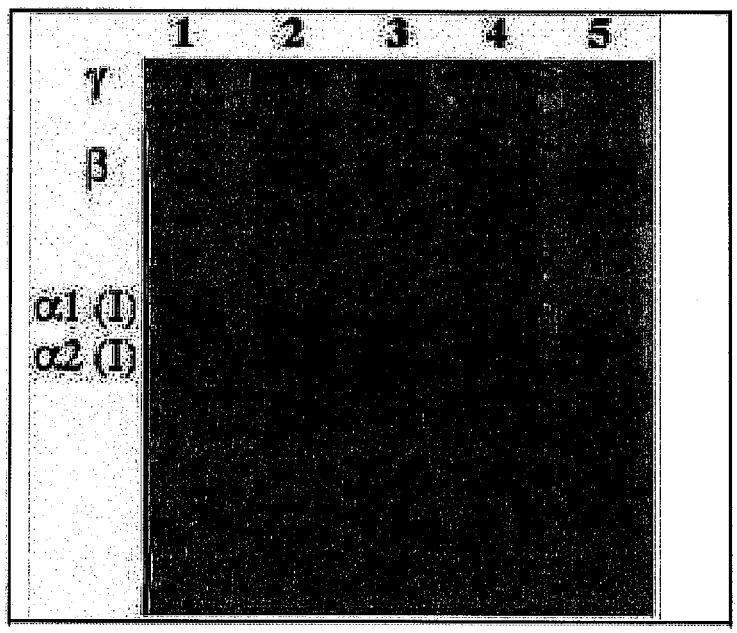
FIG. 1 is an image of a SDS-PAGE gel of Collagel® and Purecol®.

The invention is directed to the unexpected finding that a hydrogel comprising a telopeptide-collagen and an atelopeptide-collagen will not gel, or have a reduced gelation rate, at room temperature. The inventive hydrogels generally begin gelling when the mixture is heated.

The inventors have discovered mixtures and methods capable of controlling the gelation rate via cross-link blocking peptides. There are four cross-linking sites on collagen molecules, one in each amino and carboxy telopeptide and two others at sites in the triple-helical domains at or close to residues 87 and 930. N- and C-telopeptide are the N- and C-terminal 11- to 26-residue nontriple-helical domains of tropocollagen, which are involved in fibrillogenesis and cross-linking. The C-terminal telopeptide is important for initiating proper fibrillogenesis. The inventors have discovered that a peptide that can block the cross-linking site on the C-terminal telopeptide will reduce the gelation rate of a telopeptide-collagen.

In one aspect, the invention is a hydrogel comprising 5-25 weight percent of a telopeptide collagen and 75-95 weight percent of an atelopeptide collagen. Alternatively, the hydrogel comprises 80-95 weight percent, 85-95 weight percent, 75-90 weight percent, or 80-90 weight percent of the atelopeptide-collagen. In another alternative embodiment, the hydrogel comprises 5-20 weight percent, 5-15 weight percent, 10-25 weight percent, or 10-20 weight percent of the telopeptide-collagen. These weight percentages are based on the total amount of collagen in the hydrogel.

Type I collagen is a fibrous protein that contributes to the strength and other unique physiological functions of connective tissues in skin, tendon, bone and cartilage. As a structural protein, collagen is essential for the body's physical structure and for the extracellular matrix. It provides a supporting framework to cells and other matrix components such as proteoglycans and polysaccharides. The native collagen molecule is composed of three intertwined peptide chains with about 3,000 amino acids. Collagen molecules are capable of self-assembly into well oriented fibrils in vivo and in vitro when the telopeptide ends are intact, especially the C-terminal, fibril associating sequence. In the body, however, collagen is directed to form higher-ordered structures according to their locations. In addition, intermolecular cross-linking occurs within and between triple helices, serving to increase the tissue mechanical strength and biochemical stability. Collagen telopeptide, the non-helical ends of the native molecule, are critical in the process by guiding collagen molecules to assemble into microfibrils, providing intermolecular cross-linking sites and interacting with other matrix components. Recent collagen fibril modeling has demonstrated that there are two critical domains in the assembled fibrils: 1) a cell interaction domain that spans the overlap region of assembled collagen molecules and 2) matrix binding domains such as the α1β1 and α2β1 integrin binding sites that involve a -GF-PGER-(Seq. ID No. 1) peptide sequence. Furthermore, modeling data indicates that collagen fibrils must be formed in order for cells to bind to the proper cell interaction locations on collagen fibrils.

Currently, most collagens are obtained from bovine bone, hides or tendons and widely used in the agricultural, medical, cosmetic, and research fields. Harsh extraction conditions involving heat and base or strong acid are usually used to extract collagen from bone and hides for food and agricultural purposes. However, in order to solubilize and extract maximal amounts of collagen for medical and basic science applications, a more gentle extraction procedure involving acetic acid with pepsin to hydrolyze the telopeptide and release collagen from its polymeric form are used.

Telopeptide-collagen is predominantly a type I collagen that contains intact telopeptide. In one embodiment of the invention, the telopeptide can be prepared by isolating fibrillar collagen from the Achilles tendons, specifically from herd-verified pigs (Flexcell's brand name product Collagel®). The Achilles tendons can be dissected free of muscle and bone, frozen in water and sliced in 1 mm cross-sectional pieces with a commercial meat slicer. The sliced tendons can be extracted at 4° C. with 0.5 M acetic acid and agitated, without pepsin. The extracted telopeptide-containing collagens (mainly type I collagen) can be precipitated with 0.8 M NaCl and sterilized with filtration techniques. The purity of type I collagen can be monitored with interrupted SDS-page gels and compared to that of atelopeptide-containing collagen.

Figure 9:
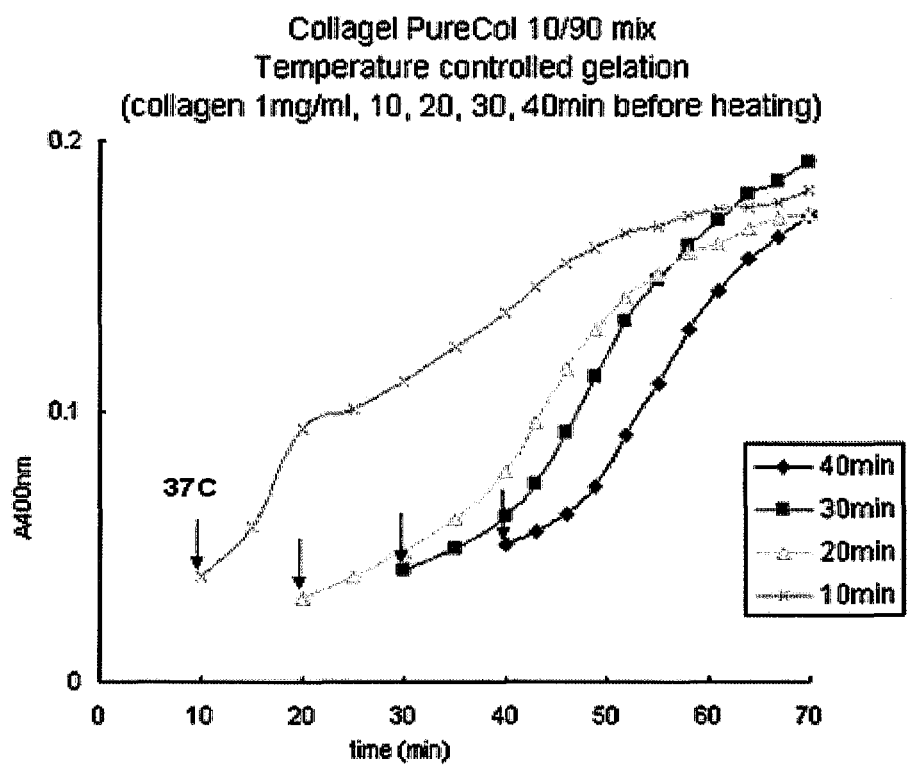
FIG. 9 is a graph showing the gelation kinetics of a Collagel®/Purecol® 10:90 mixture at 37° C.
Figure 10:
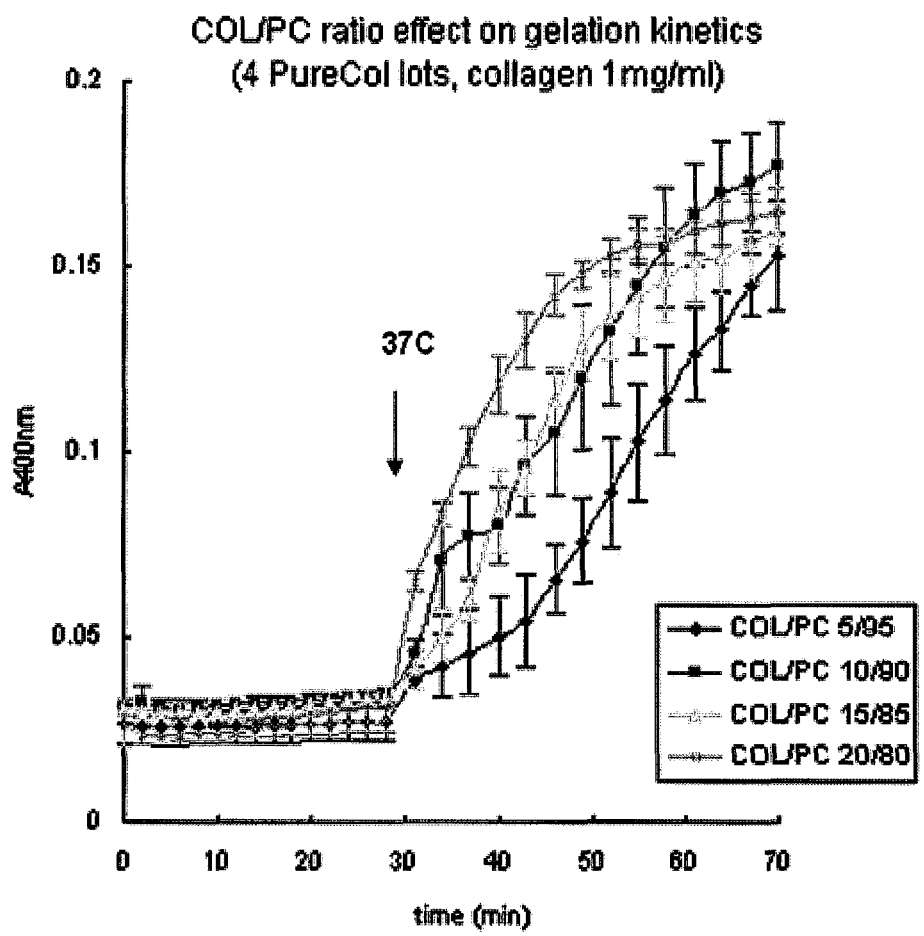
FIG. 10 is a graph showing the gelation kinetics of a Collagel®/Purecol® 5:95 to 20:80 mixtures at 37° C.
Figure 11:
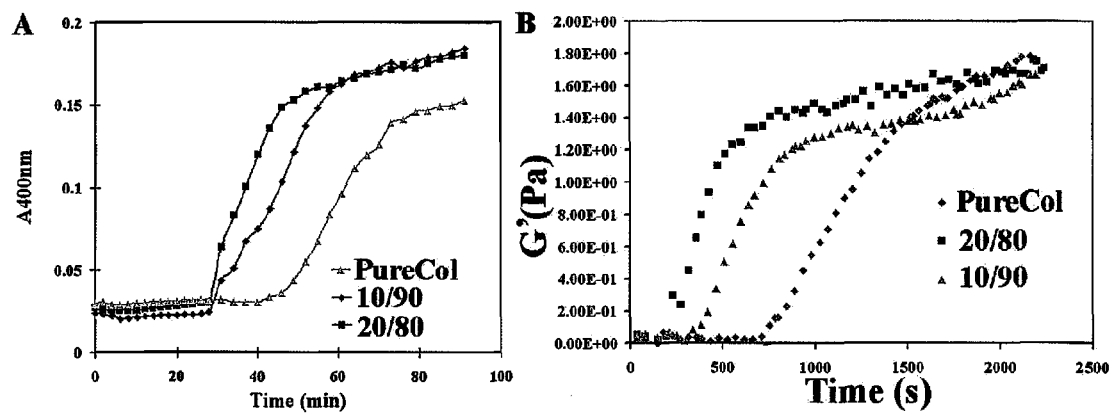
FIG. 11 is a graph showing the complete gelation, the time is approximately 10, 15 and 30 min. for 20/80 telopeptide-collagen:atelopeptide-collagen, 10/90 telopeptide-collagen:atelopeptide-collagen and PureCol®.

Atelopeptide-collagen is a collagen that contains atelopeptide. Such products are commercially available (e.g. Purecol®, Advanced Biomolecules). Atelopeptide-collagens contain at least 95% or 97%-100% by weight atelopeptide type I collagen, and less than 5% or 0-3% by weight type III collagen (see FIG. 9).

The above-described hydrogel is fabricated by combining the telopeptide-collagen and atelopeptide-collagen, thereby forming a mixture. The mixture is then heated. Preferably, the mixture is heated to a temperature of at least 37° C.

In one embodiment, the invention is a method of reducing the gelation rate of a telopeptide-collagen containing hydrogel. The method comprises mixing a telopeptide-collagen and an atelopeptide-collagen thereby forming a collagen mixture. Generally, telopeptide-collagen hydrogels will begin to polymerize at room temperature (see FIG. 5). It was unexpected to find that hydrogels that comprise a mixture of telopeptide-collagen and atelopeptide-collagen also do not polymerize at room temperature (see FIGS. 8-12). Therefore, the mixture can be stored at room temperature.

In another embodiment, the above-described hydrogel further comprises chitosan. Chitosan is a copolymer of glucosamine and N-acetylglucosamine derived from the natural polymer chitin. Chitosan is a potentially useful pharmaceutical material (drug delivery) owing to its good biocompatibility, low toxicity and biodegradability. Chitosan is a linear polysaccharide comprising β-(1-4)-linked glucosamine and N-acetyl-D-glucosamine. It is deacetylated chitin, poly (D-glucosamine). It is used as a scaffold material in tissue engineering. Chitosan-genipin gels are rigid and cannot be contracted by the entrapped cells. The inventors have found that the addition of a polysaccharide network cross-linked with type I collagen reduces the compaction rate of the hydrogel in a controllable fashion. The inventors have found that genipin-cross-linked collagen hydrogels is superior to collagen alone in both clinical and tissue engineering applications. Cells cultured on hydrogels that contained chitosan had reduced compaction rates compared to the compaction rate of cells cultured on collagen hydrogels (see FIG. 23). The chitosan may represent approximately 0.01-1 weight percent, 0.05-0.5 weight percent, 0.05-0.25 weight percent, 0.075-0.15 weight percent or about 0.1 weight percent of the mixture.

Optionally, genipin can be added to the mixture. Genipin is an aglycone, a non-sugar compound that remains after the replacement of the glycosoyl group from a glycoside. Genipin is a naturally occurring cross-linker, which has been shown to have no to low cytotoxicity. In the instant invention, genipin was used to enhance the strength of collagen polymers and to crosslink the collagen with a chitosan polysaccharide network. The mixture may contain 10-100 nM, 10-75 nM, 15-50 nM, 15-25 nM or about 20 nM of genipin.

A disadvantage limiting the application of collagen hydrogels in tissue engineering is the rapid compaction rate. Cell-seeded collagen hydrogels will compact up to 50% during the first 24 hours of gelation, which limits culturing time and may result in apoptosis. To address this problem, the inventors have developed a method of reducing the compaction rate of cells. The method comprises preparing a hydrogel collagen mixture. The mixture may comprise atelopeptide-collagen, telopeptide-collagen, or a combination of atelopeptide-collagen and telopeptide-collagen as described above. The mixture further comprises chitosan. A hydrogel is formed by allowing the hydrogel collagen mixture to polymerize. Cells are then cultured on the polymerized hydrogel, thereby reducing the compaction rate of the cells. Optionally, the hydrogel further comprises genipin.

Figure 18:
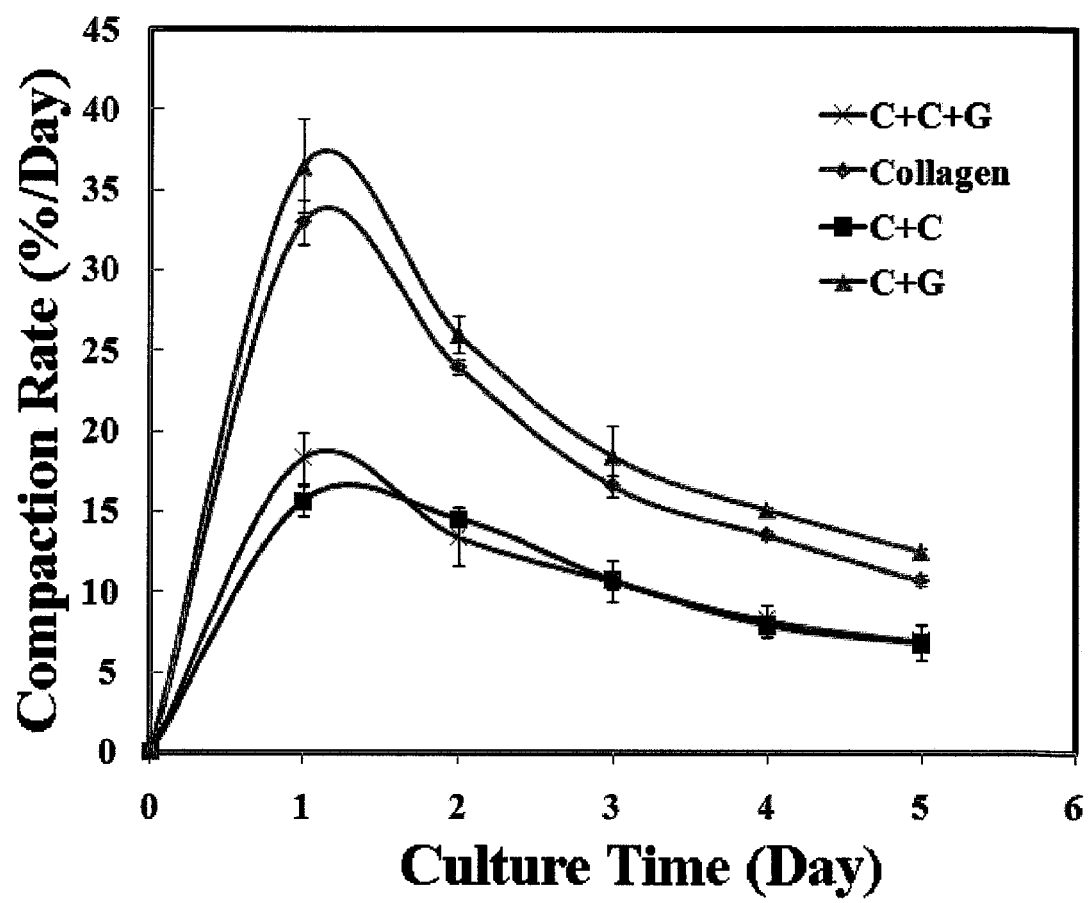
FIG. 18 is a graph showing compaction kinetics for a collagen and chitosan (C+C), collagen and genipin (C+G) and collagen and chitosan and genipin (C+C+G)
Figure 19:
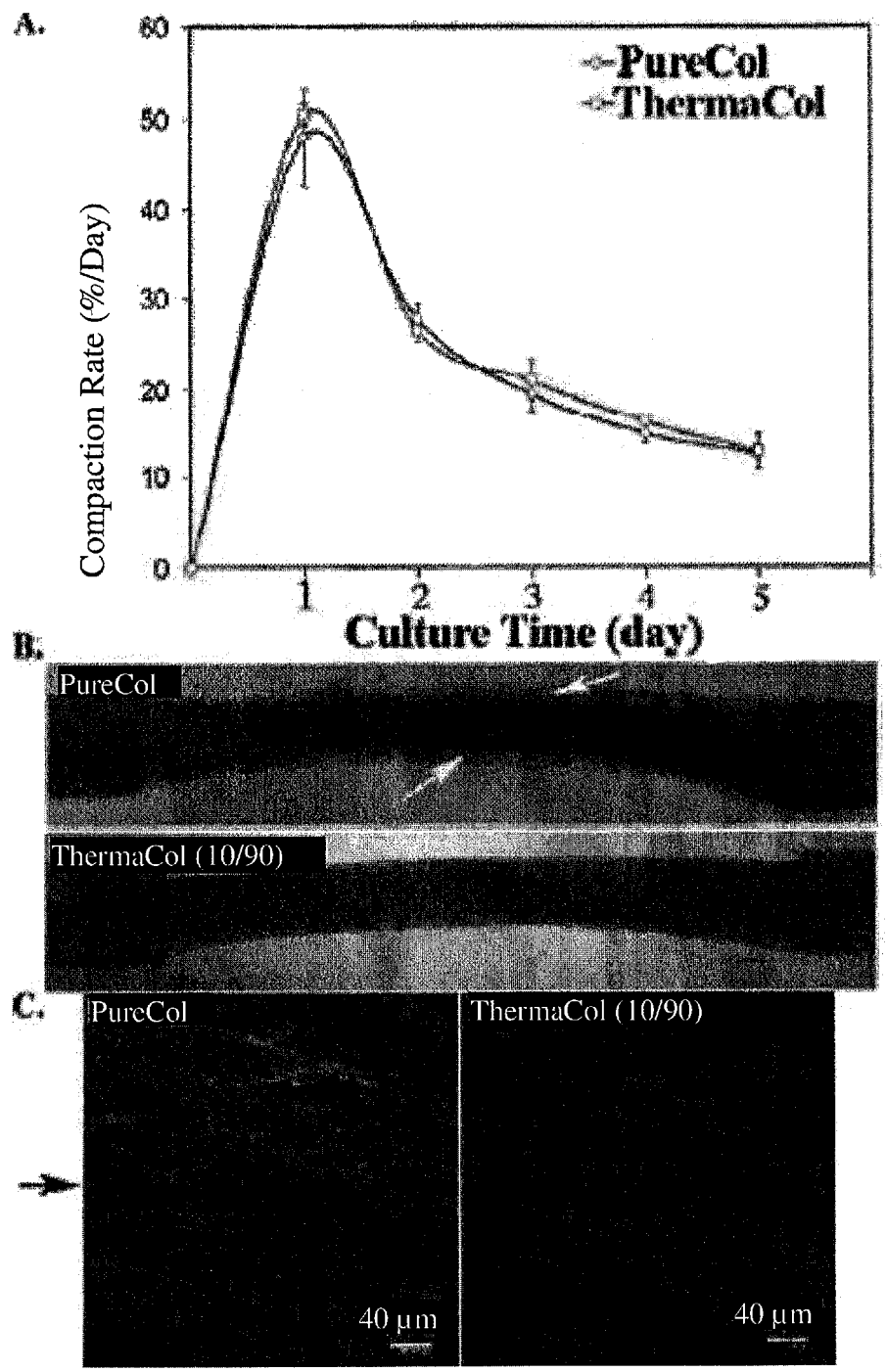
FIG. 19 illustrates the compaction of hydrogels. Panel A is the compaction curves of 10% telopeptide-collagen: 90% atelopeptide-collagen hydrogel (ThermaCol™) vs. PureCol®. Panel B is the phase contrast images of collagen gels made with PureCol® (top) or 10% telopeptide-collagen: 90% atelopeptide-collagen hydrogel (ThermaCol™) (bottom) on day 2. Arrows point to the light area. Panel C is the confocal reflection images of collagen gels on day 2. Cells were stained with rhodamine-phalloidin. Scale bar is 40 µm. The arrow in b points to the boundary between light and dark areas in the image of PureCol® seen in panel A. 10% telopeptide-collagen:90% atelopeptide-collagen hydrogel (ThermaCol™) had no inhomogeneous boundary.
Figure 20A:
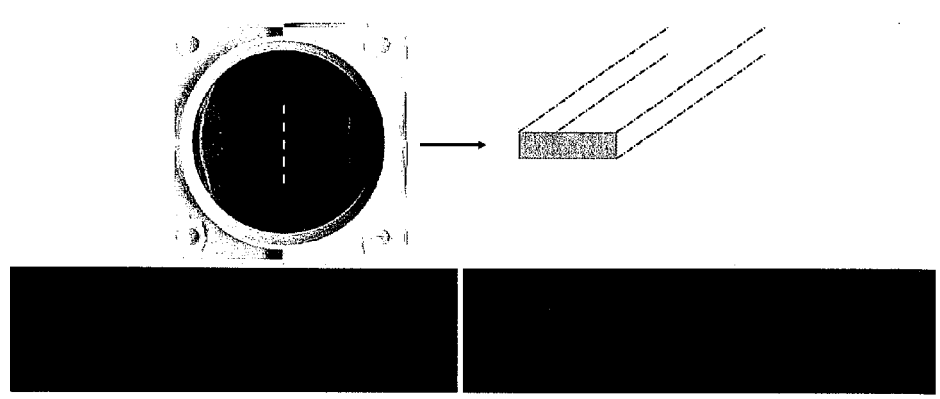
FIG. 20A-C illustrates the distribution and viability of MG63 cells in collagen gels.
Figure 20B:
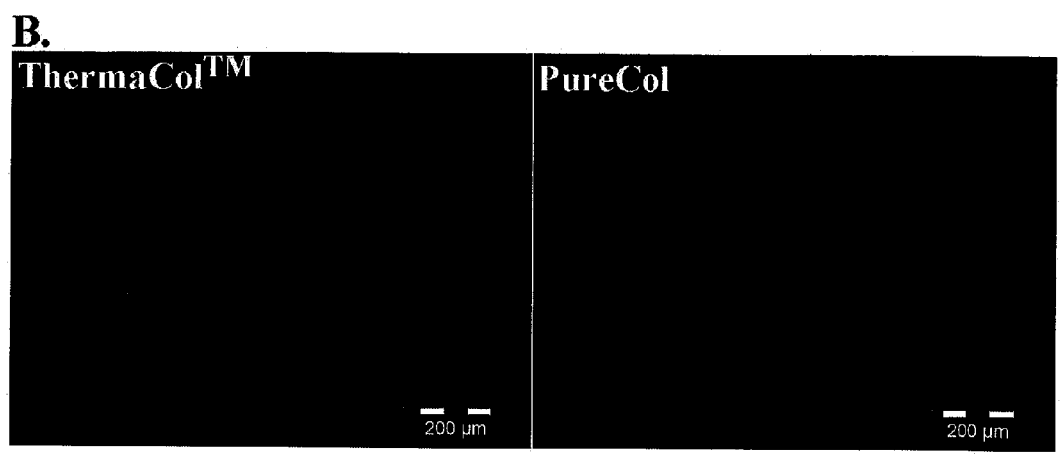
Figure 20C:
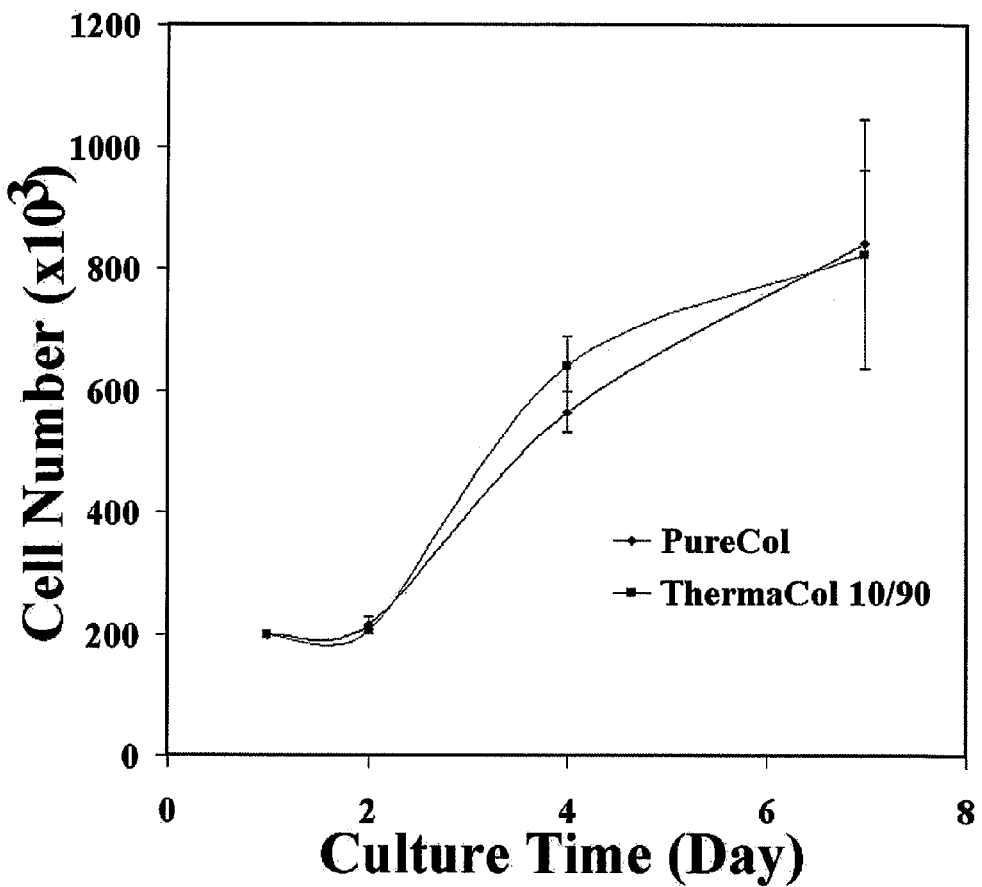
Figure 21:
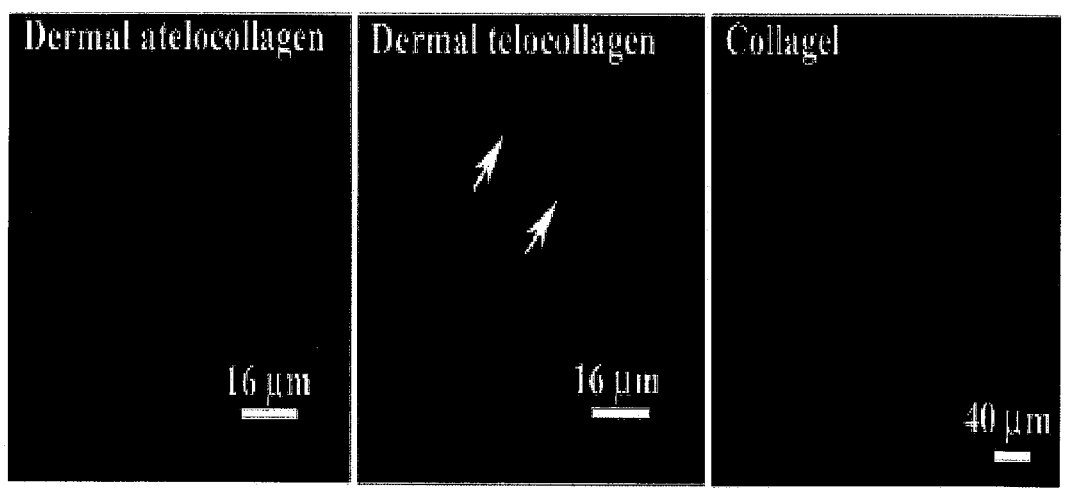
FIG. 21 illustrates confocal reflection microscopy of collagen gels. Dermal atelopeptide-collagen and dermal telopeptide-collagen (telopeptide-containing) are bovine collagens. Collagel® are porcine Achilles tendon collagen. Scale bar is 16 µm, except for that in Collagel® whose scale bar is 40 µm. A 40× oil objective with 4× zoom (except for the image of Collagel® fibers) was used.
Figure 22:
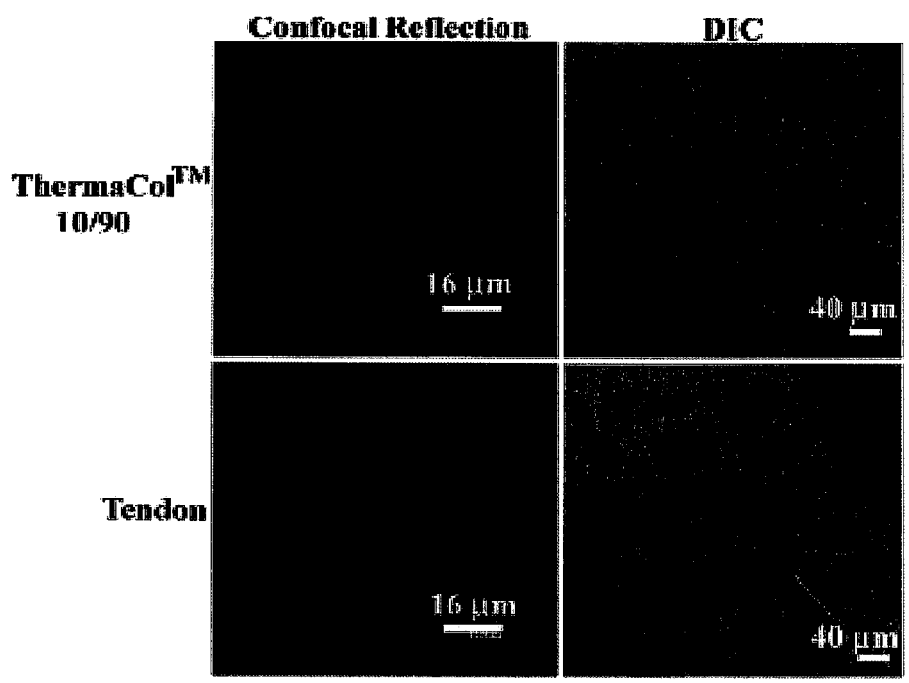
FIG. 22 illustrates the confocal reflection and DIC (Differential Interference Contrast) images of 10% telopeptide-collagen:90% atelopeptide-collagen hydrogel (ThermaCol™) (10/90) gels and human flexor digitorum profundus (FDP) tendon.

Cells cultured on hydrogels that contained chitosan and genipin had reduced compaction rates compared to the compaction rate of cells cultured on collagen hydrogels (see FIG. 18).

In one embodiment, the invention is a non-pepsin treated collagen that has a rapid gel time and long shelf life compared to other commercially available collagens for scientific and medical use, which are of the acid-soluble, pepsin-treated, genetic type I, atelopeptide variety usually isolated from bovine hides or tendon. The non-pepsin treated collagen may come from skin or tendon (e.g., Achilles tendon). As such, they are non-native, slow gelling forms lacking the fibril-associating peptide ends so that they form a weak, random fibrillar network with a pepsin residual and limited shelf life. The advantage of the inventive hydrogel over other collagen hydrogels is that it forms organized collagen fibril networks and the gelation time can be regulated so that it can be used for tissue engineering applications, such as beta pancreatic cell encapsulation, matrix scaffolds, organ development and drug delivery.

In another embodiment, the invention is a hydrogel comprising 5-20% by weight of the telopeptide-collagen and at least 71.2% by weight, at least 74.7% by weight, at least 76.0% by weight or at least 77.6% by weight of a type I atelopeptide collagen. The telopeptide-collagen may be derived from skin or tendon. The atelopeptide-collagen may be derived from skin, for example, bovine skin.

In another embodiment, the invention is a method of forming a hydrogel. The method comprises preparing a mixture comprising 5-20% by weight of a telopeptide-collagen and at least 71.2% by weight, at least 74.7% by weight, at least 76.0% by weight or at least 77.6% by weight of a type I atelopeptide collagen. The mixture is heated to at least 37° C.

In another embodiment, the invention is directed to a method of fabricating a telopeptide containing hydrogel. The method comprises combining 5-25 weight percent of a telopeptide-collagen and 75-95 weight percent an atelopeptide-collagen to form a mixture. Alternatively, the mixture may be formed by combining 80-95 weight percent, 85-95 weight percent, 75-90 weight percent, or 80-90 weight percent of the atelopeptide with 5-20 weight percent, 5-15 weight percent, 10-25 weight percent, or 10-20 weight percent of the telopeptide-collagen. These weight percentages are based on the total amount of collagen in the hydrogel. Alternatively, rather than combining an atelopeptide, the method can use at least 71.2% by weight, at least 74.7% by weight, at least 76.0% by weight or at least 77.6% by weight of a type I atelopeptide-collagen.

In another embodiment, the invention is directed to a method of reducing gelation at room temperature of a telopeptide-containing hydrogel. The method comprises combining 5-25 weight percent of a telopeptide-collagen and 75-95 weight percent of an atelopeptide-collagen to form a mixture. Alternatively, the mixture may be formed by combining 80-95 weight percent, 85-95 weight percent, 75-90 weight percent, or 80-90 weight percent of the atelopeptide with 5-20 weight percent, 5-15 weight percent, 10-25 weight percent, or 10-20 weight percent of the telopeptide-collagen. These weight percentages are based on the total amount of collagen in the hydrogel. Alternatively, rather than combining an atelopeptide, the method can use at least 71.2% by weight, at least 74.7% by weight, at least 76.0% by weight or at least 77.6% by weight of a type I atelopeptide-collagen.

In another embodiment, the invention is directed to a hydrogel comprising collagen and chitosan. The hydrogel may optionally comprise genipin. The hydrogel comprises a collagen selected from the group consisting of telopeptide-collagen, atelopeptide-collagen and a combination of telopeptide-collagen and atelopeptide-collagen. The combination of telopeptide-collagen and atelopeptide-collagen can comprise 5-25 weight percent of a telopeptide-collagen and 75-95 weight percent an atelopeptide-collagen to form a mixture; or 80-95 weight percent, 85-95 weight percent, 75-90 weight percent, or 80-90 weight percent of the atelopeptide with 5-20 weight percent, 5-15 weight percent, 10-25 weight percent, or 10-20 weight percent of the telopeptide-collagen.

In another embodiment, the invention is directed to a method of reducing cell compaction. The method comprising mixing a collagen with a chitosan to form a mixture, and allowing that mixture to form a hydrogel. The mixture may optionally comprise genipin. The collagen can be selected from the group consisting of telopeptide-collagen, atelopeptide-collagen and a combination of telopeptide-collagen and atelopeptide-collagen. The combination of telopeptide-collagen and atelopeptide-collagen can comprise 5-25 weight percent of a telopeptide-collagen and 75-95 weight percent of an atelopeptide-collagen to form a mixture; or 80-95 weight percent, 85-95 weight percent, 75-90 weight percent, or 80-90 weight percent of the atelopeptide with 5-20 weight percent, 5-15 weight percent, 10-25 weight percent, or 10-20 weight percent of the telopeptide-collagen. The method further comprises culturing cells on the hydrogel.

EXAMPLES

Dissection of Porcine Achilles Tendons and Extraction of Type I Collagen

Twenty-50 porcine Achilles tendons weighing approximately 1 kg each, were dissected. Residual muscle, bone and tendinous connective tissue was removed from the tendons. The residual connective tissue was further removed by washing tendons with phosphate buffered saline (PBS) at pH 7.2. The ratio of PBS to tendons (v/w) was 3:1 (100 mL/g). The dissected porcine Achilles tendons was frozen in $H_2O$ and sliced with a commercial meat slicer. Frozen tendons are much easier to cut and reduce denaturation induced by preparation. The sliced tendons were extracted with 0.5 M HOAc at 4° C. with agitation for 3 days. The extraction solution was changed daily and the extractants combined. The w/v ratio of wet weight of tendon to HOAc will be 1 g/100 mL HOAc. The combined extractants was filtered through 6-layers of cheese cloth to remove tendon debris then the filtered extract precipitated with 0.8 M NaCl under agitation at 4° C. overnight. The supernatant fluid was decanted, and the precipitate was dissolved in the same volume of 0.5 M HOAc at 4° C. overnight. Collagens were precipitated with 0.8 M NaCl, and the precipitate was dissolved in a half volume of 0.012 N HCl.

Figure 2:
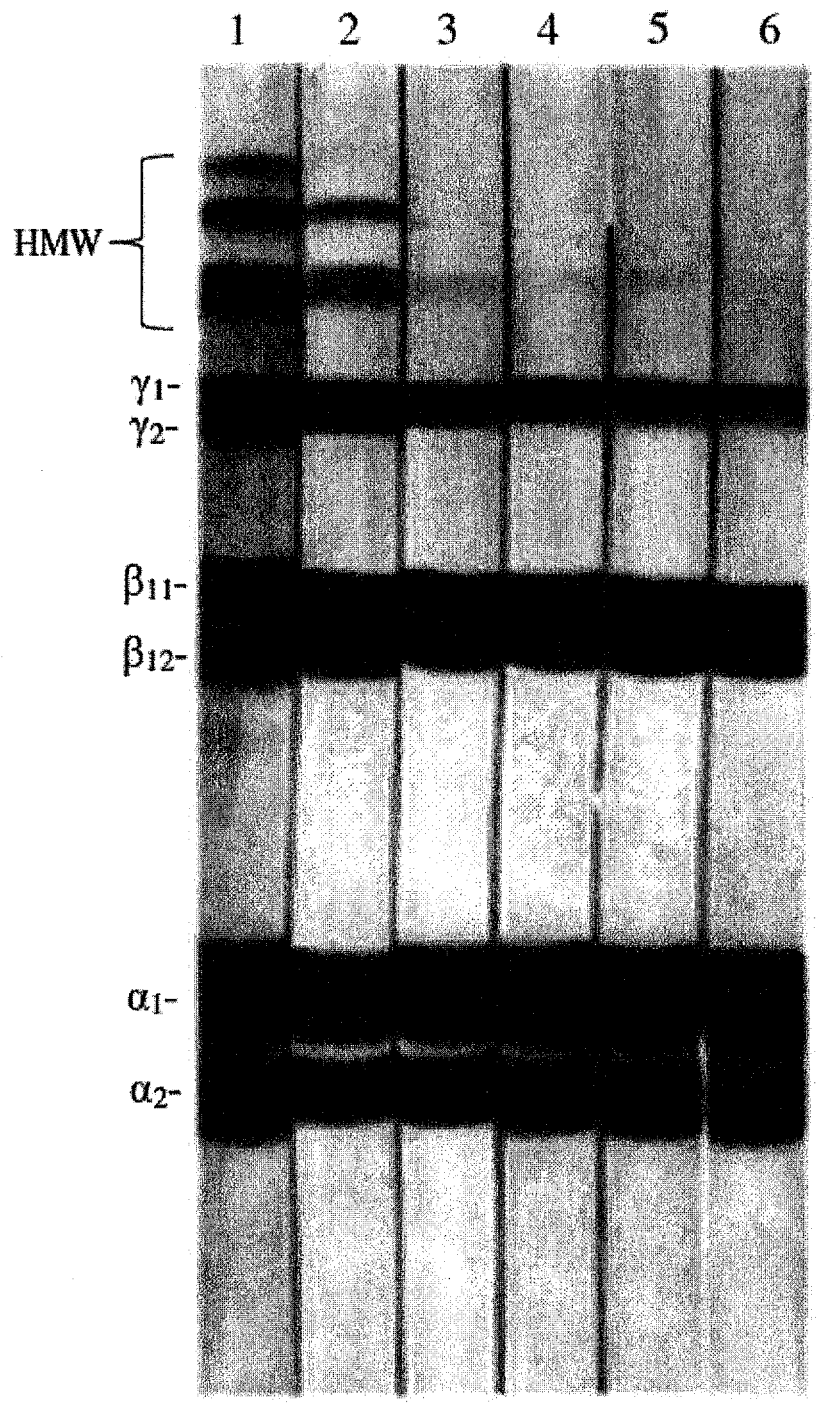
FIG. 2 is an image of a SDS-PAGE gel collagen samples that contain different amounts of oligomers. The SDS-polyacrylamide gel electrophoresis patterns of collagen samples contained different amounts of oligomer. Four percent polyacrylamide tube gels were used. The samples were first run at 6 mA/tube for 30 min and then at 3 mA/tube for 10.5 h. They were deliberately overloaded (60-90 mg/tube) to give better visualization of the high molecular weight components. Lanes 1 and 3-6 correspond to the samples 1 and 3-6 in FIG. 1. The sample in Lane 2 was similar to those of Lanes 3-6 except a collagen concentration of 0.8 mg/ml was used in purifying the monomer. The $\alpha$ and $\beta$ bands were labeled according to their conventional nomenclature. Two distinct bands were found on the gels. Since they have not been given specific names in the literature, they were labeled $\lambda_1$ and $\lambda_2$ here. The bands with molecular weights greater than that of the $\lambda_1$ and $\lambda_2$ bands were collectively labeled as HMW standing for high molecular weight components.

The purity of collagen prepared by the above-described method was determined as described in method 1.3. Six µg of proteins were loaded in each well and separated in 5% SDS-PAGE gels. Gels were stained with GelCode® Blue stain reagent (Thermo Fisher Scientific, Rockford, Ill.). Lane 1 is bovine type I collagen standard, lane 2 is atelopeptide-collagen (Purecol®) with reduction, lane 3 is atelopeptide-collagen (Purecol®), lane 4 is the collagen prepared by the above-described method with reduction and lane 5 is Collagel® (FIG. 1; see also FIG. 2).

The concentration of type I collagen was determined using a Sircol Collagen Assay kit according to manufacturer's protocol (Biocolor, Belfast, UK). The Sircol Collagen Assay kit is a quantitative dye-binding method designed for the analysis of acid-soluble collagens extracted from mammalian tissues and collagens released into culture medium by mammalian cells during in vitro culture. Briefly, 1 mL Sirius Red will be added to 100 µl of collagen samples and incubated under gentle rotation for 30 minutes at room temperature. After centrifugation for 10 minutes at 12,000×g, the collagen-bound dye (precipitate) was redissolved with 1 ml of 0.5 MNaOH, and the absorbance will be measured at 540 nm in a Nanodrop spectrophotometer (Thermo Fisher Scientific, Wilmington, Del.). The samples were measured in duplicate. To make a standard curve, 5, 10, 25 and 50 µg collagen standard was used.

Determination of the $\alpha1/\alpha2$ Ratio, $\beta$, $\gamma$ Collagen Chain Composition and Content of Type III Collagen in the Telopeptide-Collagen.

Figure 3:
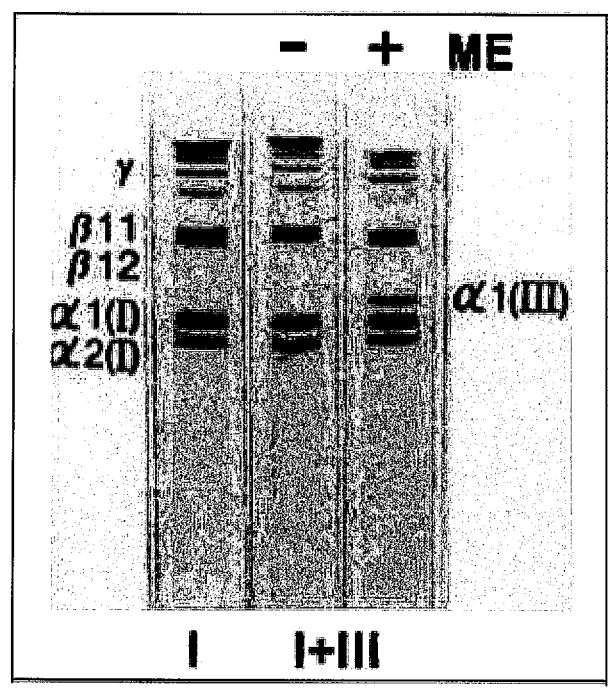
FIG. 3 is an image of a SDS-PAGE gel showing the detection of type III collagen. Detection of type III collagen by interrupted gel electrophoresis. I: type I collagen standard, I+III: precipitated collagen fraction containing type I and III, ME: 2-mercaptoethanol (10%) treatment.
Figure 4:
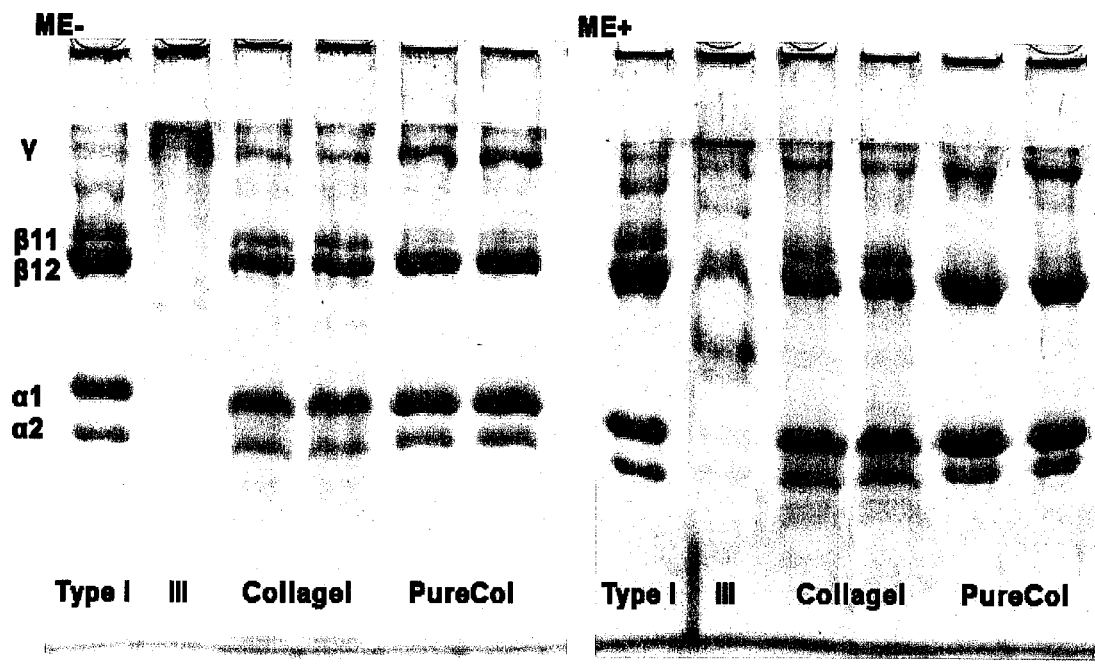
FIG. 4 is an image of a SDS-PAGE gel showing the molecular species in Collagel® and Purecol®.

The ratio of $\alpha1/\alpha2$ type I collagen chains as well as $\beta$ dimmers and $\gamma$ and higher polymers was quantitated by analyzing digital data for band strength of Coomassie blue-stained polyacrylamide gels after image capture and analysis. The content of type III collagen in Collagel® was determined with the interrupted electrophoresis method. Collagen samples were dissolved in non-reducible SDS sample buffer (5 µl/well) and separated in 5% bisacrylamide (0.1% SDS). After 1 hour with 1~1.5 cm migration, buffer from wells where the collagen samples to be reduced were removed and 10% 2-mercaptoethanol (2ME)/electrode buffer was added to the wells, incubated at room temperature for 1 hour to allow 2ME to diffuse into the gel. 2ME was removed from each well, and wells were rinsed with electrode buffer, then electrophoresis was resumed. The gel will be stained with Coomassie Brilliant Blue R250. FIGS. 3 and 4 show gels run with the interrupted electrophoresis method for type I and type III collagens with and without reduction. Here was no detectable type III collagen in Collagel® (FIG. 4).

Collagel® has a richer $\beta$ component than Purecol®, but does not contain much higher molecular weight, polymeric component. Additionally, Purecol® may contain as much as 3% type III collagen, which controls fibril diameter growth. See FIG. 4.

The mixture is a combination of 5-25 weight percent of telopeptide-collagen and 75-95 weight percent of Purecol®. Since Purecol® contains at least 95% or at least 97% type I atelopeptide-collagen, the combination includes 71.2-90.2% or 72.8.%-92.2% by weight of type I atelopeptide-collagen. The remainder of the collagen in Purecol® may be Type III collagen. Thus, the hydrogel developed by the inventors has at least 71.2%, at least 72.8.%, at least 76.0% or at least 77.6% by weight type I atelopeptide collagen.

Sterilization of Hydrogel.

The first step was to remove high polymers of collagen, which retards sterilization by filtration under pressure. This step was performed using a STAR filter system (Hilliard, S.C.) at 60 psi. This system has a total of 43.29 F2 filtration area. The flow rate was approximately 11 mL/min at 32 psi based on factory testing on Collagel® (5 mg/mL). The sterilization step was carried out with a MiniKros plus TFF system (Spectrum Laboratories, Inc., Rancho Dominguez, Calif.). This system was autoclavable and can process up to 200 liters of solution in 6 hours. Endotoxin contamination will be assessed using a GenScript Toxin Sensor Chromogenic LAL *Limulus amebocyte* assay kit (GenScript endotoxin manual). Verification of sterility was performed by neutralizing replicate samples (n=4) from each lot as for cell culture use (see below) and incubating at 37° C. for 3 days. Media was plated from each sample on blood agar plates and in nutrient broth cultures and assessed for contamination by turbidity and Gramm's staining and observation of the slides.

Gelation kinetics.

Extraction of type I collagen from tendons is a mature technique. The most popular techniques involve the extraction of collagen with weak acids (0.5 M acetic acid, HOAc) and precipitation of type I collagen with NaCl. The intent 1 is to prepare two, 20 L batches of Collagel® for subsequent use in the experiments. Two 5 L batches have been prepared and are in use in current experiments.

Figure 5:
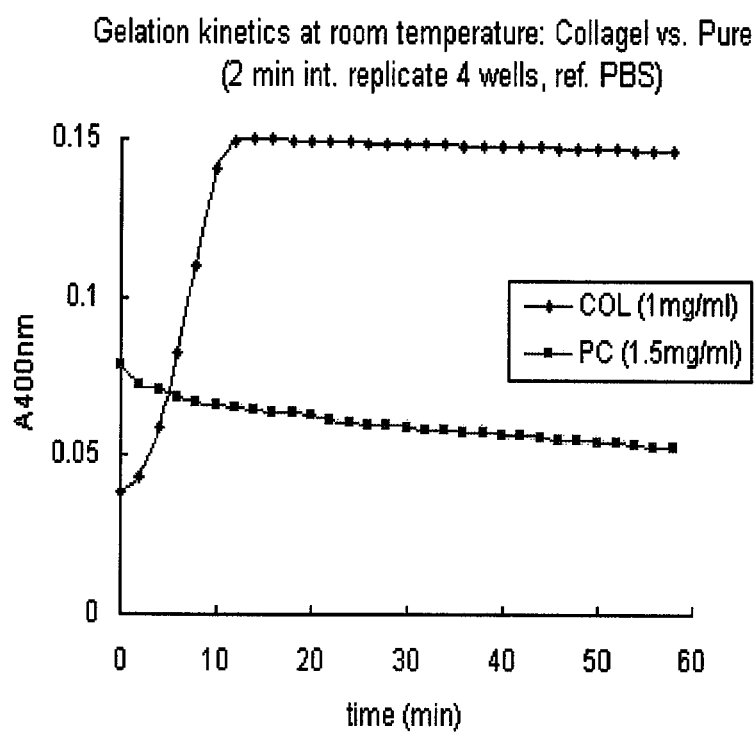
FIG. 5 is a graph of the gelation kinetics of Collagel® and Purecol®. The concentrations of Collagel® and Purecol® are 1.0 mg/ml and 1.5 mg/ml, respectively.

Telopeptide-collagen at 2.1 mg/mL will gel instantly when neutralized (FIG. 5). In order to measure the gelation kinetics of telopeptide-collagen, a lower concentration of collagen was used (1.0 mg/mL). Atelopeptide-collagen does not gel at room temperature at 1.5 mg/mL. The result shows a much shorter lag time (<1 min) compared to Purecol® (~10 min at 2.1 mg/mL, 37° C.) (FIG. 5).

Figure 6:
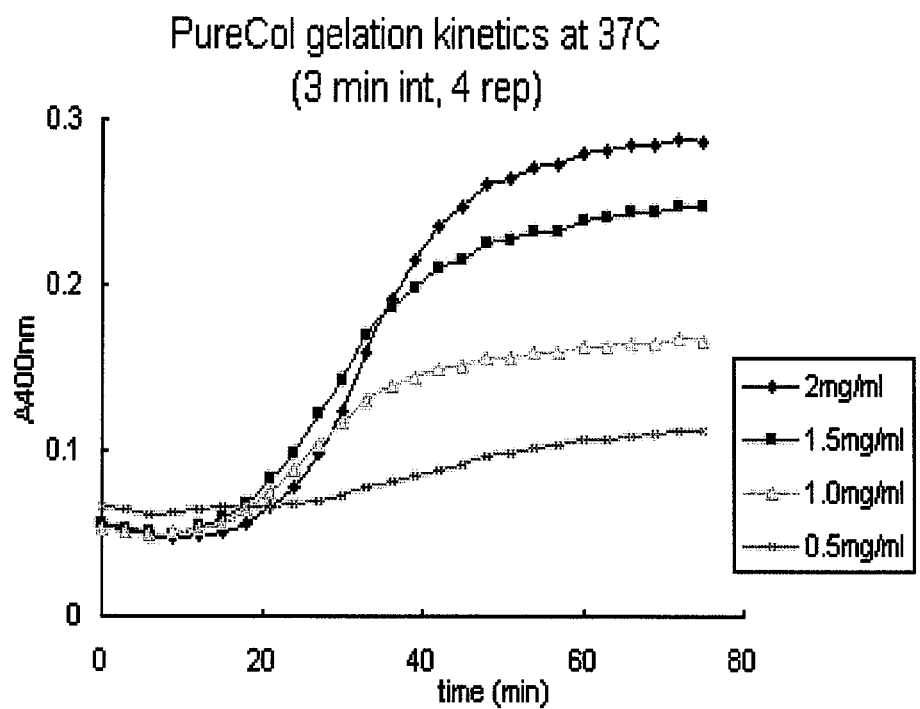
FIG. 6 is a graph showing the gelation kinetics of Purecol® at 37° C.

Collagen with telopeptide (such as Collagel®) can form fibrils at room temperature, and begin gelation within 10 minutes (FIG. 5). After about 20 minutes at 37° C., atelopeptide-collagen begins to gel (FIG. 6).

Figure 7:
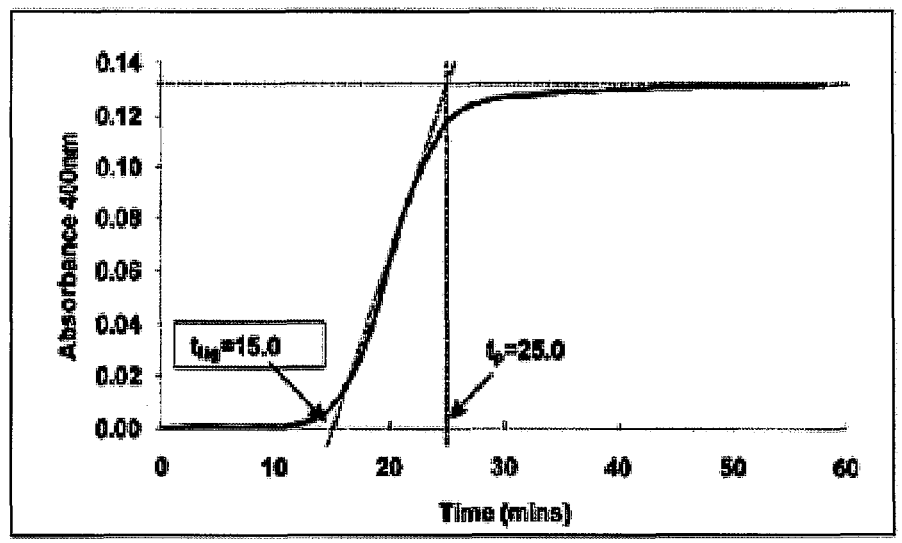
FIG. 7 is a graph of collagen gelation kinetics.

Fibrillogenesis kinetics of telopeptide-collagen alone (Collagel®, Flexcell International Corp., Hillsborough, N.C.) and telopeptide-collagen (Collagel®, Flexcell International Corp., Hillsborough, N.C.) doped with chitosan (0.1, 0.15, 0.2 and 0.25%) and genepin (10, 50 100 µM) was monitored turbidimetrically by absorbance at 400 nm and compared to that of an atelopeptide-containing collagen such as Purecol® (n=6/samples per lot; initial lot and two additional lots to be tested). 100 µL samples from each group were added at 4° C. to each well of a 96-well plate and measurements were taken at 2 min intervals for up to 3 h in a microplate reader (Modulus microplate reader, Turner Biosystems) at room temperature. The lag time (tlag) is defined as the intersection of a tangent to the linear growth portion of the curve with the time axis. The plateau time (tp) is defined as the intersection between a tangent to the plateau phase of the curve and the tangent to the linear growth portion of the curve. During the early lag phase, aggregation occurs, primarily by linear addition of collagen molecules to form end-overlapped or four dimensional (4D)-staggered dimers and trimers for fibrillogenesis. The absorbance levels at the plateau phase are indicative of the thickness of the stable fibrils formed, with increased thickness resulting in a higher absorbance at 400 nm (see FIG. 7).

The combination of telopeptide-collagen and atelopeptide-collagen creates a collagen hydrogel where gelation is induced thermally. Although not wishing to be bound by theory, the inventors believe that the telopeptide-dependent characteristic alignment for nucleation and fibril growth and the tissue-specific collagen molecular composition, i.e. high molecular oligomeric collagen rich in tendon collagen are contributing factors to the thermally induced gelation of the mixture.

A small amount of intact telopeptide from Collagel® may provide nucleation sites to initiate gelation when combined with atelopeptide-collagen. Telopeptide intact tendon collagen in a mixture may also affect fibril growth pattern. Free telopeptide alone do not have this function as the collagen mixture in one solution gradually loses its gelation characteristics in days and weeks, where the residual pepsin may have cleaved telopeptide from the telopeptide-collagen molecules (FIG. 8).

Figure 8:
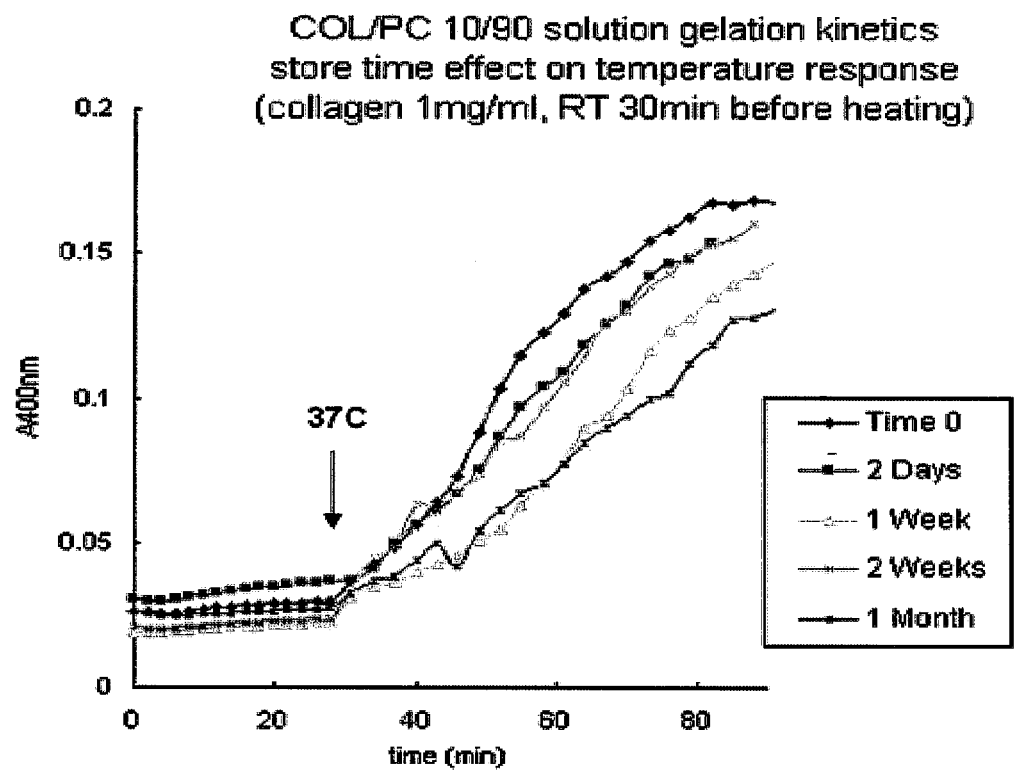
FIG. 8 is a graph showing the gelation kinetics of a Collagel®/Purecol® 10:90 mixture at 37° C. after the mixture was stored at room temperature.

Thermacol™, which is a mixture of telopeptide-collagen and atelopeptide-collagen as described above, did not form a gel or form fibrils at room temperature (FIG. 8). Upon heating Thermacol™ to 37° C., gelation was initiated immediately and fibrils grow within 20 minutes. This occurs for mixtures of Collagel® to Purecol® ranging between 5-25% Collagel® and 75-95% Purecol® (FIGS. 8-12). At 25% Collagel® and 75% Purecol®, gelation begins at room temperature.

Figure 13:
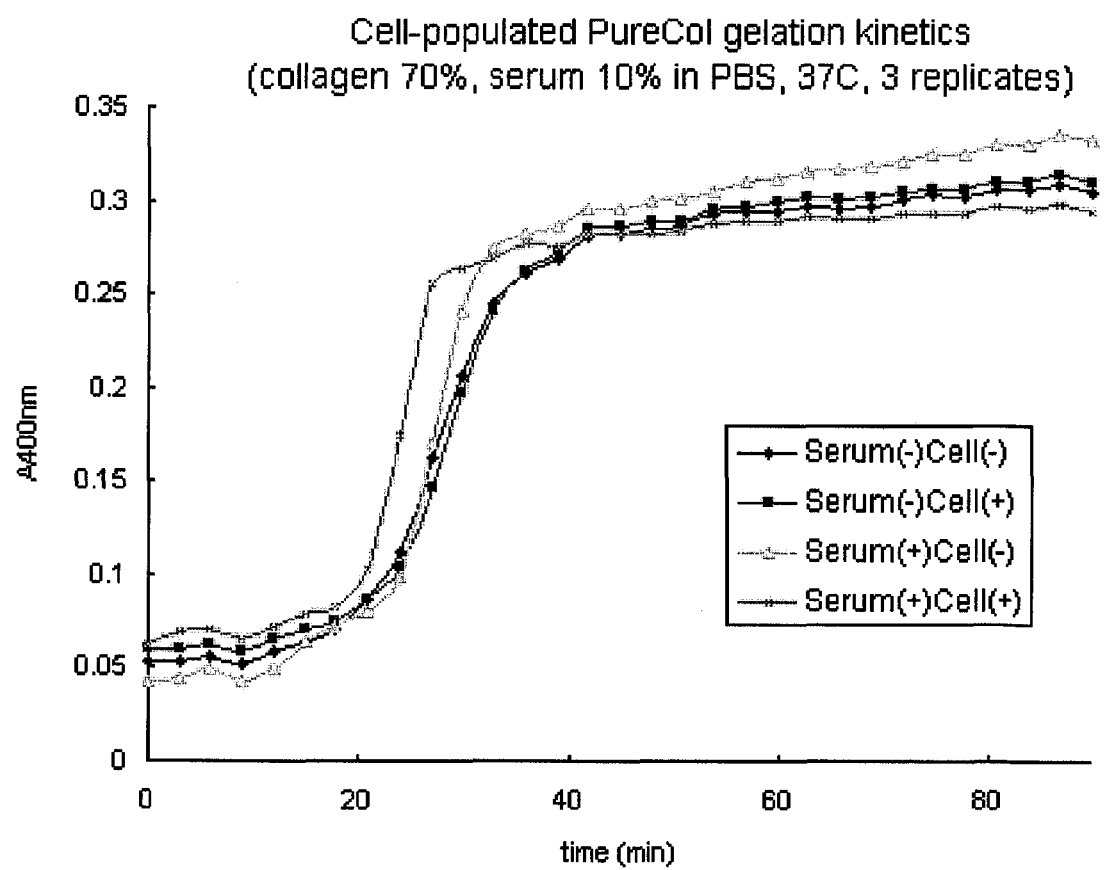
FIG. 13 is a graph showing the gelation kinetics of 70% Purecol® with cells in serum (10%).
Figure 14:
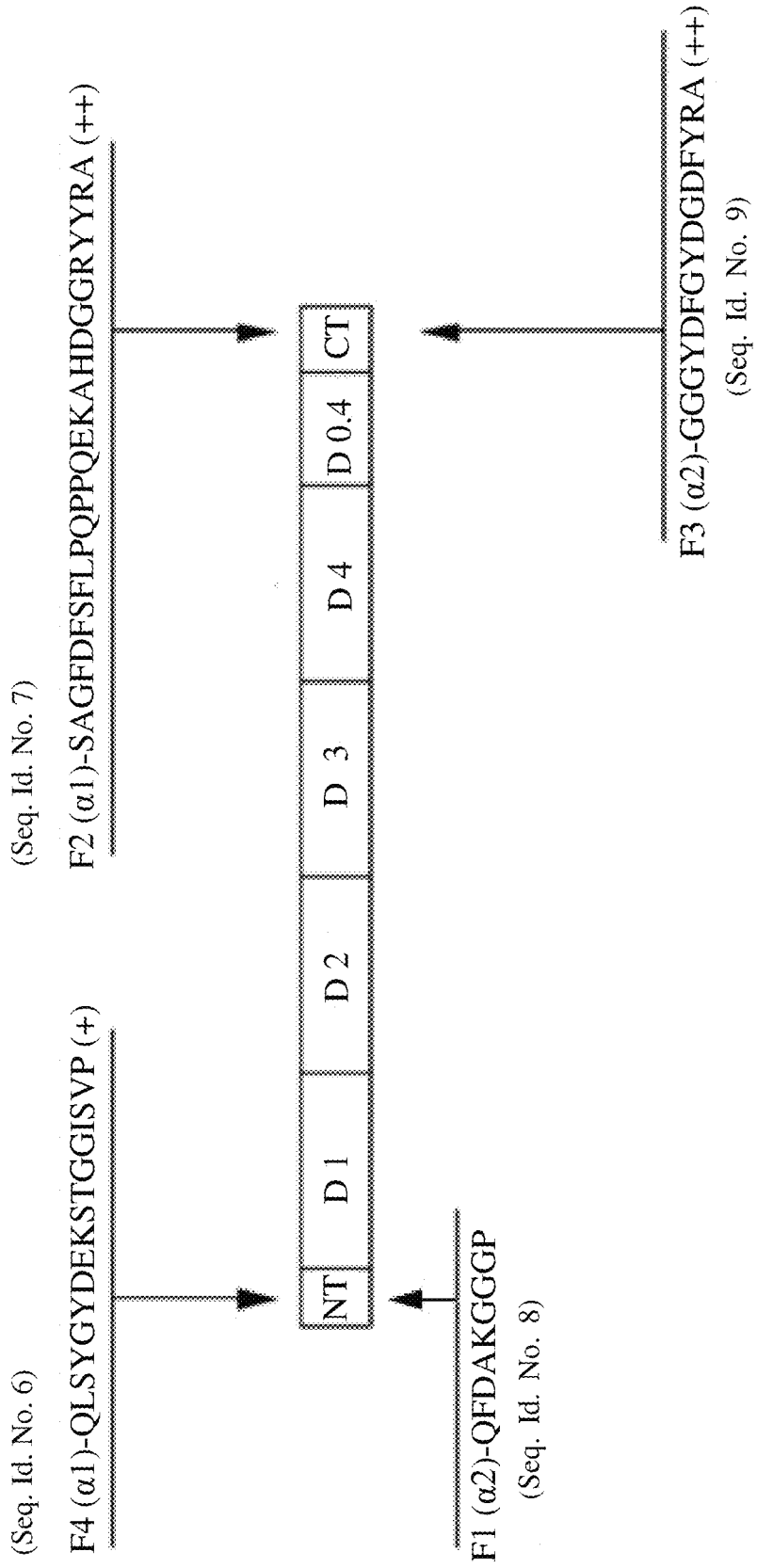
FIG. 14 is a diagram of the telopeptide binding inhibition.

The addition of cells does not change the gelation kinetics. Cells or serum was added to Purecol® (70%). The addition of cells, serum, or cells and serum did not impact the gelation kinetics at 37° C. (see FIG. 13).

Figure 12:
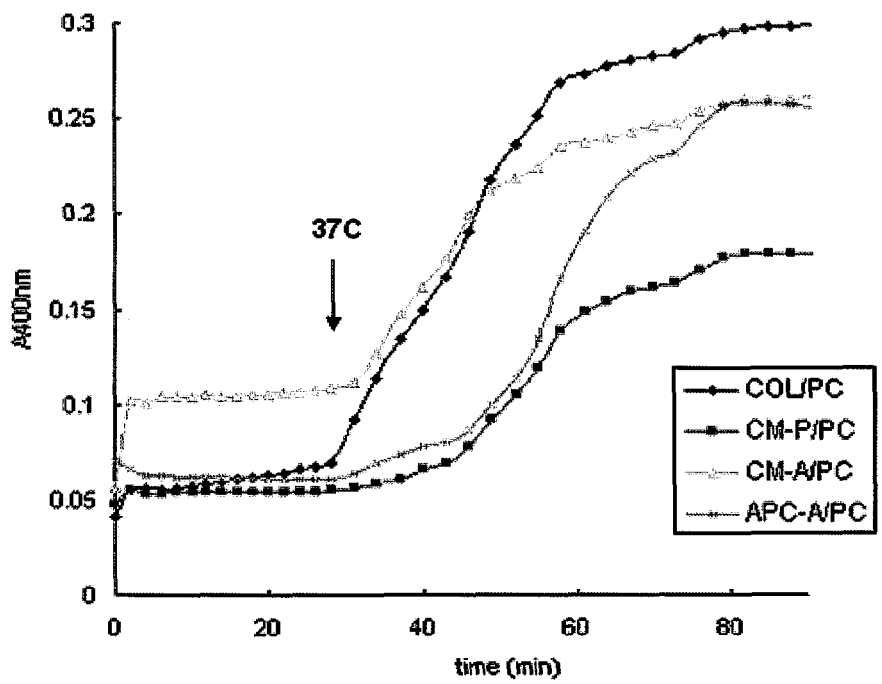
FIG. 12 is a graph showing the gelation kinetics of a 10% telopeptide-collagen/90% atelopeptide-collagen mixture at room temperature. "Col/PC" stands for 10% Collagel®/90% Purecol®. "CM-A/PC" stands for 10% Cellmatrix telopeptide-intact tendon collagen/90% Purecol®. "APC-A/PC" stands for 10% APCOLL telopeptide intact skin collagen/90% Purecol®.
Figure 15:
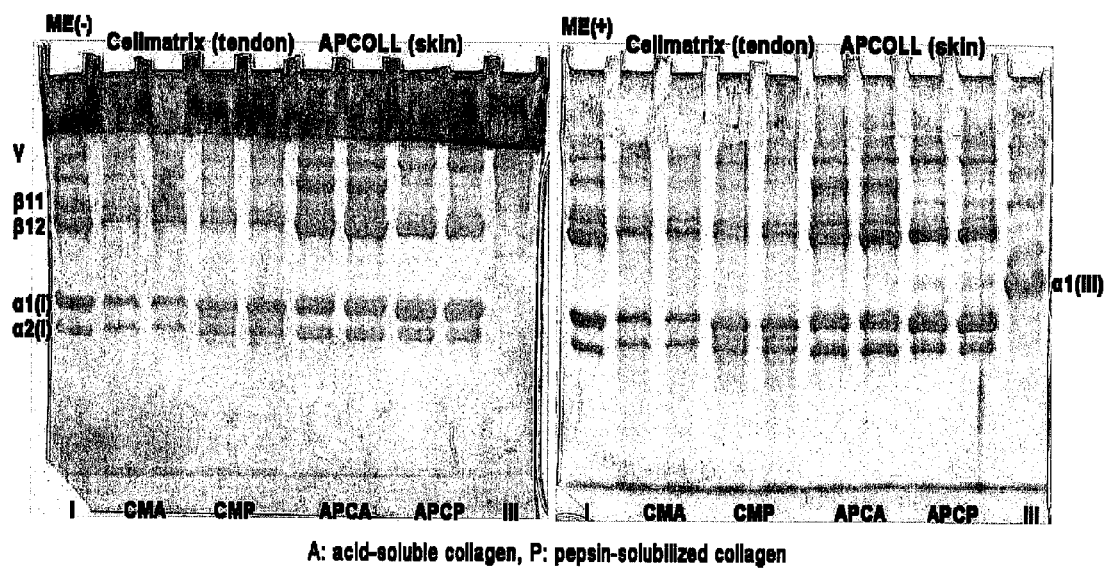
FIG. 15 is an image of two SDS-page gels showing collagen molecular species alpha, beta, and gamma chains in Cellmatrix telopeptide-intact tendon collagen CMA, cell matrix pepsin-treated atelopeptide collagen (CMP), APCOLL telopeptide-intact skin collagen (APCA), APCOLL pepsin-treated skin collagen (APCP) and Type III collagen.
Figure 16:
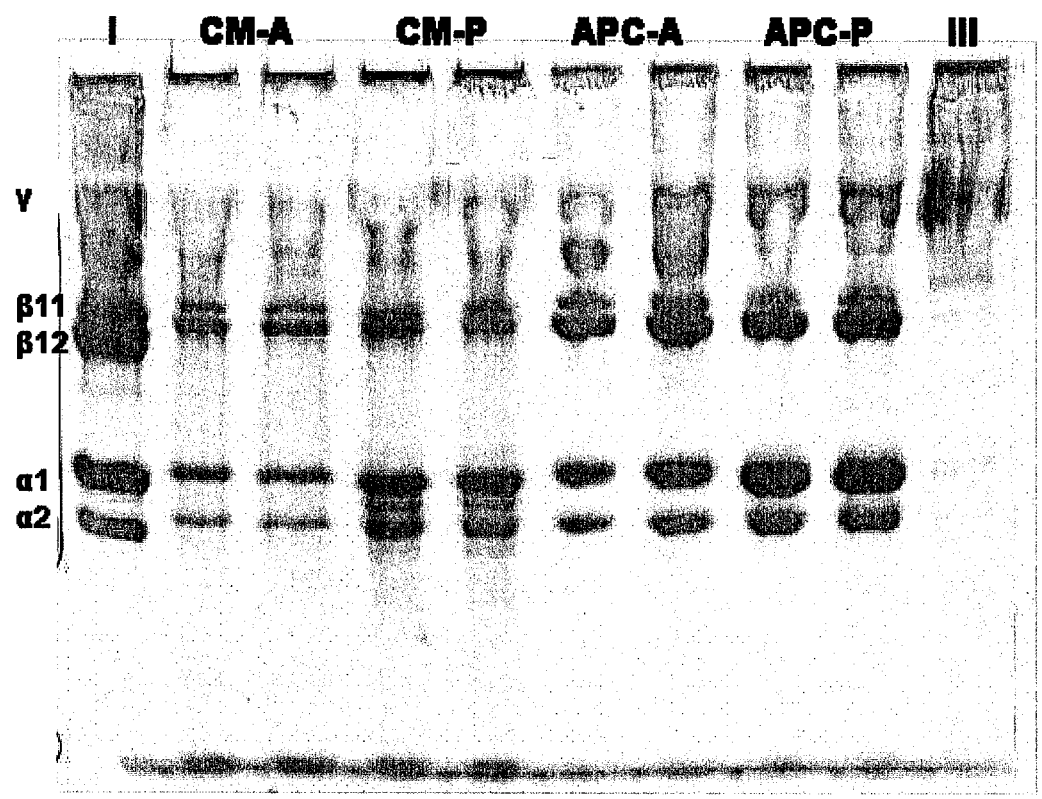
FIG. 16 is an image of a SDS-PAGE gel showing the collagen molecular structure of acid soluble and pepsin-solubolized Cellmatrix and APCOLL collagen.

Collagen can be used from other sources as well (FIG. 12). For example, Cellmatrix telopeptide-intact tendon collagen have extra α1 and α2 units (FIGS. 15-16). APCOLL skin collagen has a detectable amount of Type III collagen (FIGS. 15-16).

Cell Compaction Rates.

Figure 17:
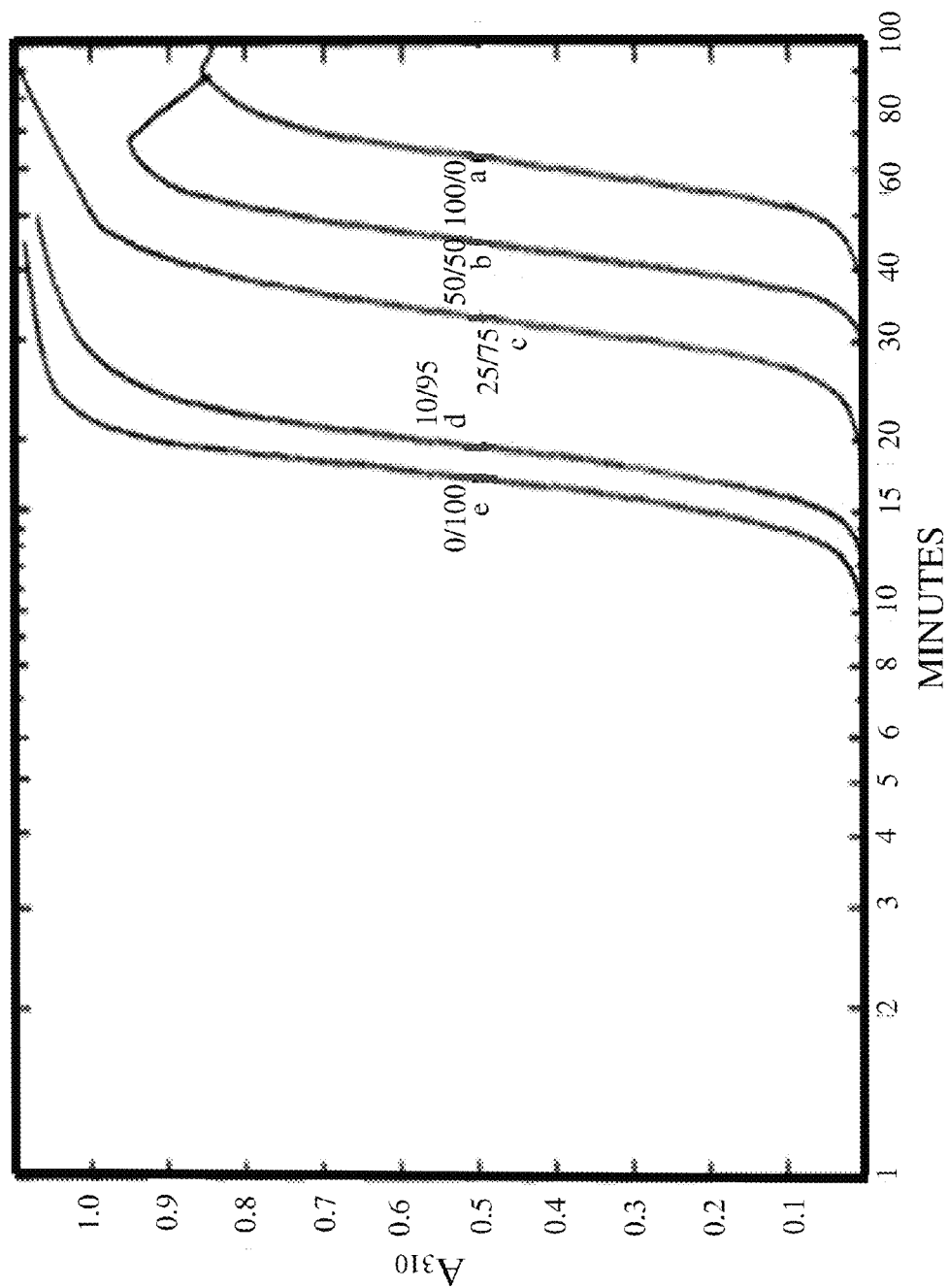
FIG. 17 is a graph illustrating data from a PronColl: AcC mixing experiment.

Linear 3D hydrogels were fabricated from telopeptide-collagen (Collagel®, Flexcell International Corp., Hillsborough, N.C.) alone and doped with chitosan (mg/ml) and genepin (mg/ml) in a Tissue Train® 3D culture system (Flexcell International Corp., Hillsborough, N.C.) as described by and compared to that of an atelopeptide-containing collagen such as Purecol®. Optimum concentrations of chitosan and genipin were selected based on the gelation kinetics data and mechanical testing from experiments (see FIG. 17).

Briefly, hydrogels were mixed with 5×MEM medium and 10% FBS and neutralized to pH 7.0 with 1 M sodium hydroxide. One hundred thousand adipose-derived human stem (hASC) cells per 100 µL of hydrogel mixture were suspended and apportioned into each well of a Tissue Train® culture plate (Flexcell International). Linear, tethered, 3D cell-populated matrices were formed by placing the Tissue Train® culture plate atop a four-place gasketed baseplate with planar-faced cylindrical posts inserted into centrally located, rectangular cutouts (six-place Loading Station™ with Trough Loaders™ (Flexcell International)) beneath each flexible well base. The Trough Loaders™ have vertical holes in the floor of the rectangle through which a vacuum is applied to deform the flexible membrane into the trough. The trough provides a space for delivery of cells and matrix. The baseplate was transferred into a 5% $CO_2$, humidified incubator at 37° C., where the construct is held in position under vacuum for 1.5 hours until the cells and matrix form a gelatinous material connected to the anchor stems. The hydrogels are then covered with growth medium (3 mL/well). The concentrations of chitosan and genipin were optimized based on the data of gelation rate and mechanical testing. The stock concentration of chitosan (Protasan UP G213, a water-soluble chitosan from Novamatrix, Norway) was 2.5 wt % in medium. The stock concentration of genipin is 20 µM in DMSO. Four concentrations of chitosan tested previously (0.1%, 0.15%, 0.2% and 0.25%) acted as the starting point from which the optimal concentration was selected. The concentrations of genipin (10, 50 and 100 nM) tested previously acted as the starting point from which an optimal concentration was selected. Five hydrogel groups were compared: group 1 (Collagel® only), group 2 (Collagel®+chitosan), group 3 (Collagel®+genipin), group 4 (Collagel®+chitosan+genipin) and group 5 (Purecol®).

Constructs would then be flooded with growth medium and placed in the incubator. Media will be changed on days 1, 3 and 6. The compaction data was collected with an automated imaging collection system, ScanFlex™ (Flexcell International Corp., U.S. Pat. No. 6,721,667). Briefly, up to four Tissue Train® culture plates were placed on a scanner in a $CO_2$ incubator, images of hydrogels were collected every two hours until the end of experiments. The areas of hydrogels were measured using SigmaScan Pro 5.0 (SPSDS Inc., Chicago, Ill.). The compaction rate is calculated as $\upsilon=(S_0-S_t)/S0*100\%/t$, where $S_0$ is the gel area at time zero, $S_t$ is the gel area at time t, and t is culture time (day). Compaction data of linear constructs from Collagel® alone was compared with those of the chitosan and genepin-doped hydrogels (FIG. 18).

On day 7, the hydrogels were tested for Young's modulus and ultimate tensile strength (UTS), determined using a patented two camera system developed by Flexcell International Corp. Six hydrogels from each group will be excised from Tissue Train® culture plates and clamped in specially constructed fixtures that grip the nylon anchors at each end of a hydrogel. The bottom clamp was connected to the load cell and will remain stationary. The top clamp was moved upward at a strain rate of 0.1 mm/second. The grip-to-grip distance between the 2 clamps will be 7.5 mm, and the excursion distance was 10 mm. Two cameras placed at 90 degrees to each other will be used to capture specimen images from which the cross-sectional area of hydrogels will be calculated. The elastic modulus (the slope of the stress-strain curve, which is proportional to the stiffness), UTS and maximum strain (at the failure point) was determined based on the stress-strain curve data.

At the end of the lag phase and during the growth phase, lateral aggregation of the initial dimers and trimers formed during the lag phase occurs, resulting in the formation of fibrils. Genipin and chitosan reduced the plateau time and increase gel strength compared to Purecol®. The gelation rate was retarded to controlled with the use of cross-link blocking peptides such as candidate peptides are EKAHDGGR (SEQ. I.D. No. 2), GGGYDFGYD (SEQ ID No. 3), GYDGDFYRA (SEQ I.D. No. 4) and SYIRIADTNIT (SEQ. I.D. No. 5). Control of gelation rate will mainly depend on the efficiency of the blocking peptides. If the competitive inhibition by using similar sequences as that of C-terminal telopeptide is not effective, some other small molecule inhibitors can be designed to block the reaction between the telopeptide aldehyde group and free amino group from the side chain of amino acid residues. The results indicated that chitosan retards the gelation and cell compaction of a telopeptide-collagen hydrogel (see FIG. 18). Chitosan can reduce the compaction of cell-populated atelopeptide-collagen hydrogels. This effect is likely due to competition for cell binding sites or interference with fibril formation. The addition of chitosan in the hydrogel may also affect the gelation rate due to the introduction of an additional free amino group. Therefore, re-optimization of genipin concentration may be necessary. Nevertheless, compaction rate can be altered by the addition of cell friendly matrix components that likely will extend the usable time in culture for cells in the gels. This is an important point to the tissue engineering field.

The invention has been described with reference to the preferred embodiment. Obvious modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A method of hastening gelation at room temperature of a telopeptide containing hydrogel comprising: providing a telopeptide-collagen; adding an atelopeptide-collagen thereby forming a collagen mixture wherein the telopeptide-collagen is 5-25 weight percent of total collagen and wherein the atelopeptide-collagen represents 75-95 weight percent of the total collagen; storing the mixture at a temperature that is less than about 37° C., wherein the mixture has hastened gelation.

2. The method according to claim 1, wherein the atelopeptide-collagen is 80-95 weight percent of the total collagen in the collagen mixture.

3. The method according to claim 1, wherein the telopeptide-collagen is 5-20 weight percent of the total collagen in the collagen mixture.

4. The method according to claim 1, wherein the atelopeptide-collagen is 75-90 weight percent of the total collagen in the collagen mixture.

5. The method according to claim 1, wherein the atelopeptide-collagen is 80-90 weight percent of the total collagen in the collagen mixture.

6. The method according to claim 1 further comprising wherein the atelopeptide-collagen comprises less than 3 weight percent of a type III collagen.

7. The method according to claim 1 further comprising adding chitosan to the collagen mixture.

8. The method according to claim 7 further comprising adding genipin to the collagen mixture.

* * * * *

SEQUENCE LISTING

```
<160> NUMBER OF SEQ ID NOS: 5

<210> SEQ ID NO 1
<211> LENGTH: 6
<212> TYPE: PRT
<213> ORGANISM: Homo sapiens

<400> SEQUENCE: 1

Gly Phe Pro Gly Glu Arg
1               5

<210> SEQ ID NO 2
<211> LENGTH: 8
<212> TYPE: PRT
<213> ORGANISM: Artificial Sequence
<220> FEATURE:
<223> OTHER INFORMATION: Cross-link blocking peptide

<400> SEQUENCE: 2

Glu Lys Ala His Asp Gly Gly Arg
1               5

<210> SEQ ID NO 3
<211> LENGTH: 9
<212> TYPE: PRT
<213> ORGANISM: Artificial Sequence
<220> FEATURE:
<223> OTHER INFORMATION: Cross-link blocking peptide
```

```
<400> SEQUENCE: 3

Gly Gly Gly Tyr Asp Phe Gly Tyr Asp
1               5

<210> SEQ ID NO 4
<211> LENGTH: 9
<212> TYPE: PRT
<213> ORGANISM: Artificial Sequence
<220> FEATURE:
<223> OTHER INFORMATION: Cross-link blocking peptide

<400> SEQUENCE: 4

Gly Tyr Asp Gly Asp Phe Tyr Arg Ala
1               5

<210> SEQ ID NO 5
<211> LENGTH: 11
<212> TYPE: PRT
<213> ORGANISM: Artificial Sequence
<220> FEATURE:
<223> OTHER INFORMATION: Cross-link blocking peptide

<400> SEQUENCE: 5

Ser Tyr Ile Arg Ile Ala Asp Thr Asn Ile Thr
1               5                   10
```